United States Patent [19]

Jessup

[11] Patent Number: 4,917,694
[45] Date of Patent: Apr. 17, 1990

[54] SURGICAL SPONGE

[75] Inventor: James L. Jessup, Elk Grove Village, Ill.

[73] Assignee: The Kendall Company, Boston, Mass.

[21] Appl. No.: 867,000

[22] Filed: May 20, 1986

Related U.S. Application Data

[63] Continuation of Ser. No. 379,683, May 19, 1982, abandoned.

[51] Int. Cl.⁴ .............................................. A61F 13/16
[52] U.S. Cl. .................................................... 604/362
[58] Field of Search ................. 604/362; 128/155, 156

[56] References Cited

U.S. PATENT DOCUMENTS 3,911,922 10/1975 Kliger ................................... 604/362
4,068,666 1/1978 Shiff ..................................... 128/156
4,205,680 6/1980 Marshall .............................. 128/156

FOREIGN PATENT DOCUMENTS 948387 6/1974 Canada ................................. 604/362
0736685 9/1955 United Kingdom .
0794352 4/1958 United Kingdom .
0839451 6/1960 United Kingdom .

Primary Examiner—C. Fred Rosenbaum
Assistant Examiner—Sharon Rose
Attorney, Agent, or Firm—Powell L. Sprunger

[57] ABSTRACT

A surgical sponge comprising, a sheet of absorbent material. The sponge has an elongated visually detectable element at a visible location on the sheet comprising a pair of elongated twisted strands. One of the strands has a color which contrasts with the color of the sheet, and the other of said strands has a color which contrasts with the color of blood.

13 Claims, 1 Drawing Sheet

SURGICAL SPONGE

This is a continuation of application Ser. No. 379,683 filed May 19, 1982, now abandoned.

BACKGROUND OF THE INVENTION

The present invention relates to absorbent articles, and more particularly to surgical sponges.

Surgical sponges are commonly used during surgical procedures to absorb body fluids of the patient both inside the incision and around the site of surgery. Sponges of this nature are usually made of an open-meshed absorbent fabric, such as woven cotton.

It is important, of course, that all of such sponges be removed from the patient's body after surgery is complete and before the incision has been closed. Accordingly, it is a standard procedure for the surgical team to carefully count the sponges both before placement in the incision and after removal from the incision to reduce the possibility that a sponge may be left in the patient.

In spite of such safety measures, sponges have been occasionally lost, particularly when an unexpected emergency disrupted the normal operative routine such as counting, which is subject to human error. When saturated by body fluids, such as blood, the sponges become significantly reduced in size and assume a color the same as some types of body tissue, thus making visual detection of the sponges extremely difficult. As a result, it has been required to provide the sponges with a flexible insert which is opaque to X-rays. In case of a disputed or nontallying sponge count in the operating room, or in case of unexpected or unexplainable post-operative discomfort on the part of the patient, a portable X-ray unit is brought to the patient and an X-ray exposure should reveal the presence or absence of a lost sponge. A negative plate should be reassurance to the surgeon that he and his operative team have not left a sponge in the patient. Nevertheless, it is desirable that the patient be provided additional assurance a sponge does not remain in his body, and that the number of instances an X-ray is necessary be minimized, whether or not additional surgery would ultimately be required to remove a lost sponge.

SUMMARY OF THE INVENTION

A principal feature of the present invention is the provision of a surgical sponge of simplified construction which prevents mishaps in reclaiming sponges from a patient's body.

The sponge of the present invention comprises, a sheet of absorbent material. The sponge has an elongated visually detectable element at a visible location on the sheet comprising a pair of elongated twisted strands. One of the strands has a color which contrasts with the color of the sheet, and the other of the strands has a color which contrasts with the color of blood.

A feature of the present invention is that the one strand enhances visibility of the element during counting of the sponges prior to placement in an incision in order to verify that the elements are in fact located on the sponges.

Another feature of the invention is that the other strand significantly increases the visibility of the sponge in a patient's body when saturated by body fluids.

Thus, a feature of the present invention is that the element minimizes the possibility that the sponge may be left in a patient's body during an operation.

Another feature of the invention is the provision of an apparatus to form the visually detectable element on the sheet.

Further features will become more fully apparent in the following description of the embodiments of this invention and from the appended claims.

DESCRIPTION OF THE PREFERRED EMBODIMENTS

Figure 3:
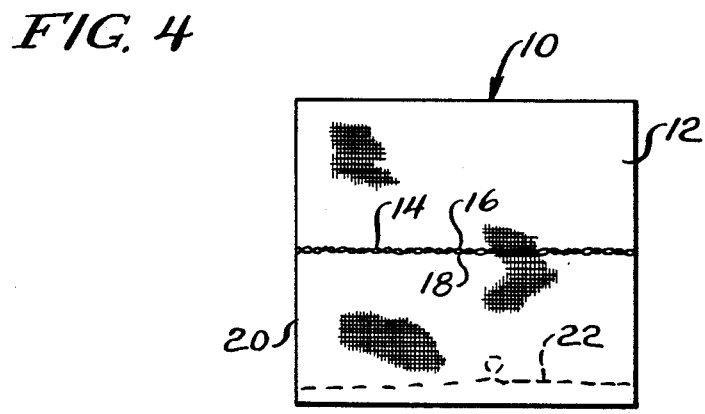
FIG. 3 is a plan view of the surgical sponge of the present invention.

Referring now to FIG. 3, there is shown a surgical sponge generally designated 10 comprising a sheet 12 of an absorbent material, e.g., a low-count open-mesh gauze or washed gauze fabric, such as woven cotton. The sheet 12 has a plurality of folds defining a multiple ply configuration of the sponge 10.

The sponge 10 has an elongated visually detectable element 14 comprising a pair of twisted strands 16 and 18 which have different colors. One of the strands 16 has a color which contrasts with the color of the sheet 12, and the other of the strands 18 has a color which contrasts with the color of blood for a purpose which will be described below. In one form, the one strand 16 may have a color such as blue or green, and the other strand 18 may have a color such as white. The strands 16 and 18 may be constructed from a blood repellant material such as polyvinylchloride. In a preferred form, the element 14 is heat-bonded to an inner surface of an outer layer 20 of the folded sheet 12 such that the element 14 is visible through the open-mesh sheet 12, thus reducing the possibility of scratching of delicate tissue by the element 14. In one form, the strands 16 and 18 may be impregnated with barium sulphate in order to make the strands 16 and 18 radiopaque. In an alternative form, the strands 16 and 18 are not radiopaque, and the sponge 10 may have a separate radiopaque element 22 located in the folded sheet 12, such as by impregnating the element 22 with barium sulphate.

Figure 1:
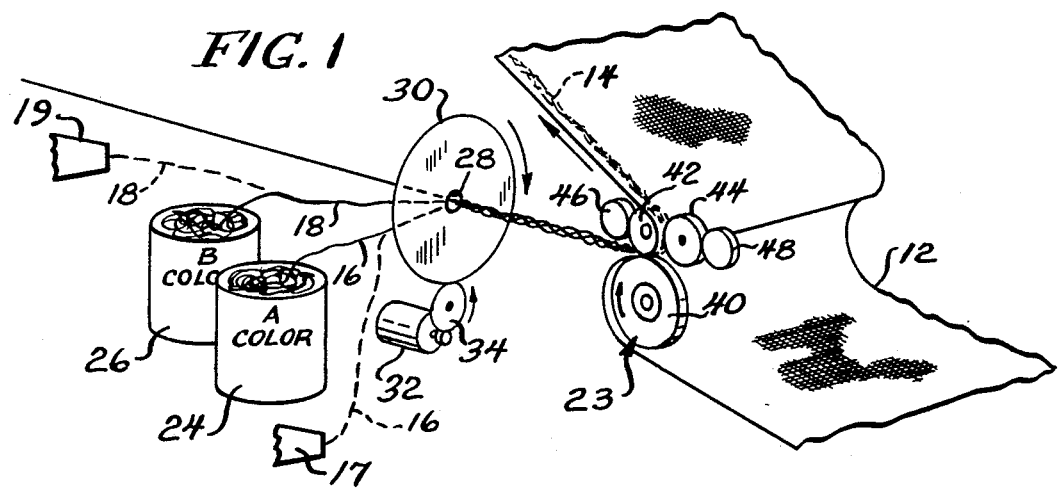
FIG. 1 is a diagrammatic view illustrating an apparatus to form the surgical sponge of the present invention.
Figure 2:
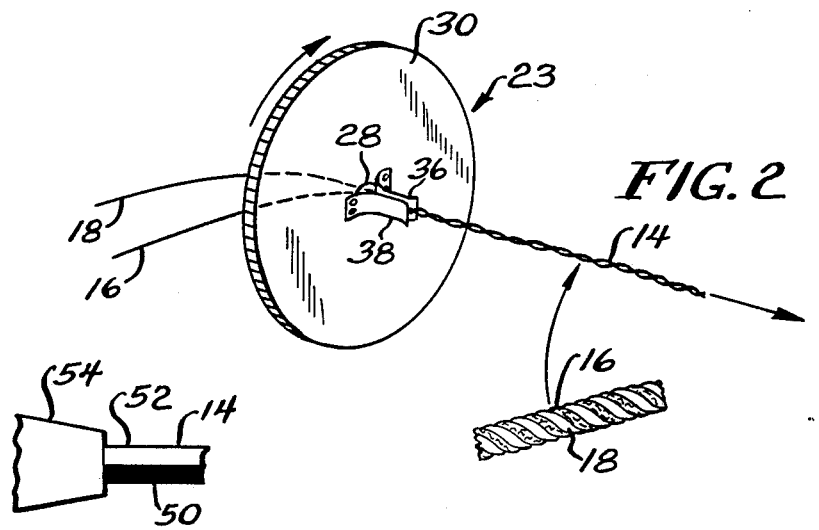
FIG. 2 is a diagrammatic view on an enlarged scale illustrating a rotating guide wheel in the apparatus of FIG. 1.

An apparatus 23 for forming the visually detectable element 14 on the sheet 12 is illustrated in FIGS. 1 and 2. As shown, the apparatus 23 has a source 24 of the first strand 16, such as a bin, and a source 26 of the other strand 18, such as a bin. The strands 16 and 18 are removed from the sources 24 and 26, respectively, and are passed through a central opening 28 in a rotating guide wheel 30. In an alternative form, the strands 16 and 18 may be extruded from extruders 17 and 19, respectively, and may be passed to the guide wheel 30. The guide wheel 30 may be driven by a suitable motor 32 and an intermediate rotatable wheel 34 which is driven by the motor 32.

With reference to FIG. 2, the guide wheel 30 has a pair of spring clips 36 and 38 which are biased together. As shown, after the strands 16 and 18 pass through the opening 28, the strands 16 and 18 are frictionally and slidably received between the clips 36 and 38 which twist the strands 16 and 18 about each other into the element 14.

With reference to FIGS. 1 and 2, the sheet 12 is passed over a rotatable wheel 40, and then between a rotatable anvil wheel 42 and a rotatable bonding wheel 44 which pull the sheet 12 between the wheels 42 and 44. The anvil wheel 42 may be driven by a suitable device such as a motor 46. The bonding wheel 44 may be driven and heated by a suitable device such as a motor and heating device 48. Thus, the sheet 12 is moved between the wheels 42 and 44 in a direction as indicated by the arrow in the drawings. Tee twisted strands 16 and 18 are passed from the guide wheel 30, and are placed against the sheet 12. The twisted strands 16 and 18 comprising the element 14 are then passed through the wheels 42 and 44 where the wheel 44 heats the element 14, and bonds the element 14 to one surface of the sheet 12, after which the element 14 passes with the sheet 12 from the wheels 42 and 44. Finally, the sheet 12 with the element 14 is cut and folded into the configuration of the surgical sponge 10 previously described in connection with FIG. 3.

In use, a number of the surgical sponges 10 are supplied to the personnel in an operating room for use during surgery. One of the persons on the operating team counts the sponges before placement in an incision, and also verifies that the element 14 is correctly in place on the sponges 10. In this regard, the one strand 16 with the color which contrasts with the color of the sheet 12 facilitates inspection of the existence of the elements 14 on the sponges 10. After counting of the sponges and inspection of the elements 14, the sponges 10 are placed in an incision in a patient's body during surgery. After surgery has been completed, the sponges 10 are removed from the incision, and the second strand 18 having a color which contrasts with the color of blood significantly enhances visibility of the sponges 10 in the incision in order to minimize the possibility that one of the sponges 10 may be left in the patient's body after surgery has been completed and the incision is closed.

Figure 4:
FIG. 4 is a diagrammatic view of another embodiment of the present invention.

Another embodiment of the present invention is illustrated in FIG. 4, in which like reference numerals designate like parts. In this embodiment, the element 14 has a first longitudinal part 50 of a color which contrasts with the color of the sponge, such as green or blue, and an integral second longitudinal part 52 of a color which contrasts with the color of blood, such as white. The parts 50 and 52 of the element 14 are coextruded from extruder 54. The element 14 may be passed directly to the wheels 40 and 42 of FIG. 1, thus bypassing the guide wheel 30, or may be passed through guide wheel 30 to give a barber pole effect.

The foregoing detailed description is given for clearness of understanding only, and no unnecessary limitations should be understood therefrom, as modifications will be obvious to those skilled in the art.

I claim:

1. A surgical sponge, comprising:
a sheet of absorbent material; and
an elongated visually detectable element at a visible location on the sheet comprising a pair of elongated strands twisted about each other, one of said strands having a color which contrasts with the color of said sheet to facilitate visual inspection of the element prior to the use of the sponge, and the other of said strands having a color which in the presence of blood contrasts with the color of blood to significantly increase the visibility of the sponge in a patient's body when saturated by body fluids with the color of the two strands being different from each other.

2. The sponge of claim 1 wherein said sheet comprises a multi-ply open mesh material, and in which said element is bonded to an inner surface of an outer layer of said sheet.

3. The sponge of claim 1 wherein said element comprises polyvinyl chloride.

4. The sponge of claim 1 wherein said element is impregnated with a radiopaque material.

5. The sponge of claim 1 including an elongated radiopaque element in the sponge.

6. The sponge of claim 1 wherein the colors of said strands are blue and white.

7. The sponge of claim 1 wherein the colors of said strands are green and white.

8. The sponge of claim 1 wherein said absorbent material comprises washed gauze.

9. The sponge of claim 3 wherein the colors of said strands are blue and white.

10. The sponge of claim 3 wherein the colors of said strands are green and white.

11. A surgical sponge, comprising:
a sheet of absorbent material; and
an elongated visually detectable element at a visible location on the sheet comprising first and second longitudinally extending integral parts, said first part having a color which contrasts with the color of the sheet to facilitate visual inspection of the element prior to use of the sponge, and said second part having a color which in the presence of blood contrasts with the color of blood to significantly increase the visibility of the sponge in a patient's body when saturated by body fluids with the color of said first and second parts being different from each other.

12. The sponge of claim 11 wherein said element is twisted.

13. A surgical sponge, comprising:
a sheet of absorbent material; and
an elongated visually detectable element at a visible location on the sheet comprising a pair of elongated strands, one of said strands having a color which contrasts with the color of said sheet to facilitate visual inspection of the element prior to the use of the sponge, and the other of said strands having a color which in the presence of blood contrasts with the color of blood to significantly increase the visibility of the sponge in a patient's body when saturated by body fluids with the color of said strands being different from each other.

* * * * *